United States Patent [19]

Krespan et al.

[11] Patent Number: 5,449,837
[45] Date of Patent: Sep. 12, 1995

[54] FLUORINATED METHYL ETHERS

[75] Inventors: Carl G. Krespan; V. N. Mallikarjuna Rao, both of Wilmington, Del.

[73] Assignee: E. I. Du Pont de Nemours and Company, Wilmington, Del.

[21] Appl. No.: 299,129

[22] Filed: Sep. 2, 1994

Related U.S. Application Data

[62] Division of Ser. No. 85,843, Jun. 30, 1993, Pat. No. 5,382,704.

[51] Int. Cl.$^6$ .......................................... C07C 43/313
[52] U.S. Cl. ..................................................... 568/604
[58] Field of Search ............................................ 568/604

[56] References Cited

U.S. PATENT DOCUMENTS

| | | |
|---|---|---|
| 3,637,477 | 1/1972 | Croix . |
| 3,761,524 | 9/1973 | Terrell et al. . |
| 3,862,242 | 1/1975 | Terrell . |
| 4,346,250 | 8/1982 | Satokawa et al. . |
| 4,668,830 | 5/1987 | Desbois . |
| 4,961,321 | 10/1990 | O'Neill et al. . |
| 5,026,924 | 6/1991 | Cicco ................. 568/683 |
| 5,185,474 | 2/1993 | O'Neill . |
| 5,196,599 | 3/1993 | Gilligan et al. . |
| 5,196,600 | 3/1993 | O'Neill . |

FOREIGN PATENT DOCUMENTS

| | | | |
|---|---|---|---|
| 0138095 | 4/1985 | European Pat. Off. ...... | C07C 43/11 |
| WO81/01846 | 7/1981 | WIPO .......................... | C07C 41/01 |

OTHER PUBLICATIONS

*Chemical Abstract*, 85, No. 159314g. (1976).
Fabre et al, "Thermodynamic Behavior of Alkanes in Superacid Media", *Chemical Rev.*, 82, 593 (1982).
Feiring, "Chemistry in Hydrogen Fluoride. 7. A Novel Synthesis of Aryl Trifluoromethyl Ethers", *J. Org. Chem.*, 44(16), 2907–2910 (1979).
Aldrich et al, "α-Fluorinated Ethers, II. Alkyl Fluoroalkyl Ethers", *J. Org. Chem.*, 29 (11), 306–310 (1964).
Hudlicky, M., *Chemistry of Organic Fluorine Compounds*, 2nd (revised edition), 179–180, 257 (1992).

*Primary Examiner*—Johann Richter
*Assistant Examiner*—John Peabody

[57] ABSTRACT

A process is disclosed for producing a fluorinated ether of the formula $R_2CHOCF_2A$, where A is Cl or F, and each R is H, $(CF_2)_nCl$, $(CF_2)_nF$ or $(CF_2)_nH$ (n is an integer from 1 to 10) by reacting a first reactant of the formula $R_2CHOY$ where Y is H, COF, COCl or COOCHR$_2$ (R is as defined above), a second reactant selected of the formula $CZ_2Cl_2$ or $COZ_2$ where each Z is independently Cl or F (provided that when A is Cl, the second reactant is $CZ_2Cl_2$), and HF; and recovering the fluorinated ether from the reaction products. Also disclosed are bis-ethers of the formula $(CF_3(CF_2)_m)_2CHOCF_2OCH(CF_2)_mCF_3)_2$, where m is an integer of 0 to 3, which can also be produced by the process.

4 Claims, No Drawings

FLUORINATED METHYL ETHERS

This is a division of application Ser. No. 08/085,843, filed Jun. 30, 1993, now U.S. Pat. No. 5,382,704.

BACKGROUND OF THE INVENTION

1. Field of the Invention

This invention relates to ethers containing fluorine substituents, and more particularly to fluorinated methyl ethers and processes for their production.

2. Background

Chlorofluorocarbons (i.e., compounds containing only carbon, fluorine, and chlorine) have been used for many years as refrigerants, heat transfer media, foam expansion agents, aerosol propellants, solvents and power cycle working fluids. However, there has been recent concern that chlorofluorocarbons might be detrimental to the Earth's ozone layer. Consequently, there is a worldwide effort to find alternative compounds which contain fewer chlorine substituents. Fluorinated dimethylethers have been proposed as replacements for some CFCs (see e.g., U.S. Pat. No. 5,196,600). Other fluorinated ether compounds are under consideration for various applications. There is thus an interest in fluorinated ether compounds and a need for efficient processes for their production.

SUMMARY OF THE INVENTION

This invention provides a process for the manufacture of fluorinated ethers of the formula $R_2CHOCF_2A$ wherein each R independently is selected from the group consisting of H, $(CF_2)_nCl$, $(CF_2)_nF$ and $(CF_2)_nH$, where n is an integer from 1 to 10 and wherein A is selected from the group consisting of Cl and F. The process comprises the step of reacting a first reactant of the formula $R_2CHOY$, wherein Y is selected from the group consisting of H, COF, COCl and $COOCHR_2$, and each R is as defined above, a second reactant selected from the group consisting of $CCl_4$, $CCl_3F$, $CCl_2F_2$, $COCl_2$, $COClF$ and $COF_2$ (provided that when A is Cl, the second reactant is selected from the group consisting of $CCl_4$, $CCl_3F$, and $CCl_2F_2$) and HF, and recovering the fluorinated ether from the reaction products. This invention further provides bis-ether compounds of the formula $(CF_3(CF_2)_m)_2CHOCF_2OCH((CF_2)_mCF_3)_2$, where m is an integer from 0 to 3.

DETAILS OF THE INVENTION

This invention involves reacting a first reactant of the formula $R_2CHOY$, a second reactant of the formula $CZ_2Cl_2$ or $COZ_2$ (where each Z is independently selected from Cl and F) and HF to produce a fluorinated methyl ether. Preferably, at least one R group of the first reactant is other than H. Suitable first reactants include alcohols (i.e., compounds where Y is H). Alcohol starting materials for the process of the present invention wherein the two R's are different and have the formula $(CF_2)_nF$ (i.e., the n of one R is not equal to the n of the other R) can be prepared by known methods using lithium aluminum hydride to reduce the corresponding ketones. Alcohol starting materials for the process of the present invention where one R is $(CF_2)_nF$ and the other R is H can be prepared by known methods using lithium aluminum hydride to reduce the corresponding acids. Alcohols where one R is $(CF_2)_nH$ and one R is H can be prepared by known methods by the reaction of methanol and tetrafluoroethylene as described in U.S. Pat. No. 4,346,250 and in Chem. Abst. 85:159314g. Alcohols where one R is $(CF_2)_nCl$ and one R is H can be prepared by known methods by the reaction of carbon tetrachloride and tetrafluoroethylene. The carbonate esters of the above alcohols (i.e., Y is $COOCHR_2$) can be prepared by known methods using 0.5 equivalents of phosgene (alcohol basis) and base. Chloroformate esters of the above alcohols (i.e., Y is COCl) can be prepared by known methods using at least an equimolar amount of phosgene ($COCl_2$). Fluoroformate esters of the above alcohols (i.e., Y is COF) can be prepared by known methods using at least an equimolar amount of carbonyl fluoride ($COF_2$). Preferred first reactants include those where Y is H, R is selected from H and $(CF_2)_nF$, and n is an integer from 1 to 4. $CF_3CH_2OH$ is a particularly useful first reactant.

The reaction may be run without a catalyst, and $CCl_4$ is particularly effective as the second reactant where no catalyst is added. Nevertheless, a catalyst may optionally be used for the reaction. Suitable catalysts include compounds selected from the group consisting of $SbX_5$, $AsX_5$, $TaX_5$, $BX_3$, $NbX_5$, and $PX_5$, where each X is independently selected from Cl and F. The oxides of Sb, As, Ta, B, Nb and P, which are converted to fluorides under reaction conditions, may also be used as catalysts. However, conversion of the oxides to fluorides typically produces water, which is preferably avoided.

More generally, in preferred embodiments in which a catalyst is used, especially when $CCl_4$ is not a reactant, effective catalysts are selected from halides which form solutions with HF that are stronger acids than HF itself. A method of ranking is the acidity scale from Chem. Rev., 1982, 82, 593, which shows some acidity functions, $H_f$, of fluoride combinations with HF that are of heightened acidity, including those of $SbF_5$, $AsF_5$, $TaF_5$, $BF_3$, $NbF_5$, $PF_5$. $H_f$ for HF is $-11.0$, while $H_f$ for the fluorides with catalytic activity ranges from $-22.1$ to at least $-12.6$ on this scale. Other compounds with an $H_f$ of less than $-11$ which can also be used as catalysts are $ClSO_3H$, $CF_3SO_3H$, and $FSO_3H$.

The molar ratio of HF to the $R_2CHOY$ reactant typically ranges from about 1:1 to about 50:1, and is preferably within the range of from about 3:1 to 30:1. The molar ratio of the $R_2CHOY$ reactant to the second reactant (e.g., $CCl_4$) typically ranges from about 1:2 to 25:1, and is preferably within the range of from about 1:1 to 5:1. The process of the present invention is suitably conducted at a temperature in the range of from about 75° C. to about 250° C., preferably from about 125° C. to about 175° C. The reaction time, in the presence or in the absence of catalyst, is typically from about one minute to about 24 hours, although even higher reaction times can be employed. The reaction variables (e.g., temperature and reactant ratios) can be balanced one against the other such that the reaction can be continued until the yield of fluorinated methyl ether is at least about 25 mol percent (based upon the moles of $R_2CHOY$ reactant).

One skilled in the art will recognize that water preferably should be avoided in these reactions, and in some instances can react with the second reactant (e.g., $COCl_2$) under reaction conditions. Nevertheless, limited amounts (e.g., less than about 2 mol %) can generally be tolerated. The reaction is preferably carried out in an essentially anhydrous medium.

The reaction products may be recovered by using conventional separation techniques, such as distillation. A preliminary treatment with water to remove HF, HCl and hydrolyzable by-products facilitates the purification process. Occasionally, as in the case of $CF_3CH_2OCF_3$ and $CFCl_3$ mixtures, a chemical treatment to remove $CFCl_3$ from the stable product ether is advantageous. The mixtures may be treated with bases (e.g., NaOH, $Na_2S$ and $Na_2CO_3$) in solution to remove $CFCl_3$. The fluorinated methyl ethers are stable fluids which are useful as solvents and heat transfer fluids. Low boiling compounds are being considered for use in refrigerant systems.

The chlorine substituent in products of the formula $R_2CHOCF_2A$, where at least one of said R or A group comprises Cl, may, if desired, be replaced with fluorine (e.g., using HF and $Cr_2O_3$ catalyst) or hydrogen (e.g., using $H_2$ and a hydrodechlorination catalyst) or recycled back to the ether synthesis reactor.

The reaction vessels of the process of the present invention should be constructed from materials which are resistant to the corrosive effects of hydrogen fluoride such as Inconel ™ nickel alloy and Hastelloy ™ nickel alloy.

Pressure is not critical. The pressure may range, for example, from 100 kPa (14.7 psia) to 27.6 mPa (4000 psia), and for many reactor systems is preferably 690 kPa (100 psia) to 6.9 mPa (1000 psia).

Some products and by-products of the process of this invention are considered novel. For example, one can react a first reactant of the formula $(CF_3(CF_2)_m)_2CHOH$ where m is an integer from 0 to 3 with $CCl_4$ and HF to produce a product containing not only the corresponding trifluoromethylether $(CF_3(CF_2)_m)_2CHOCF_3$, but also a novel bis-ether of the formula $(CF_3(CF_2)_m)_2CHOCF_2OCH((CF_2)_mCF_3)_2$. Thus $(CF_3)_2CHOH$ can be reacted with $CCl_4$ and HF to produce both $(CF_3)_2CHOCF_3$ and $(CF_3)_2CHOCF_2OCH(CF_3)_2$. These novel bis-ethers may be recovered using conventional techniques and used, for example, as chlorine-free solvents or heat transfer fluids.

Practice of the invention will become further apparent from the following nonlimiting Examples.

EXAMPLE 1

2,2,2-Trifluoroethyl Trifluoromethyl Ether
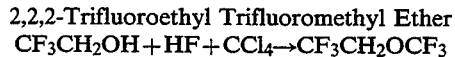

Fifty grams (0.50 mol) of $CF_3CH_2OH$, 192 g (1.25 mol) of $CCl_4$, 280 g (14 mol) of HF, and 7 g (0.1 mol) of $BF_3$ were charged to a 1.2 liter metal tube and the mixture was agitated at 150° C. and autogeneous pressure for 8 hours. The tube was cooled and 300 mL of water was pumped in. The tube was brought to room temperature and volatiles (108.6 g) were transferred under vacuum to a 1 liter stainless steel cylinder fitted with a needle valve. The contents of the cylinder were held at 25° C. while low boilers were transferred out at 1 atmosphere and distilled from $CaCl_2$ through a low-temperature still. A 2.5 mL foreshot having a boiling point range of −14° to 2.5° C., largely $CF_2Cl_2$, was followed by 62.7 g of product, boiling point range of 2.5° to 15° C. (mainly 8° to 9° C.), then 8 mL with a boiling point range of 15° to 23.5° C., largely $CFCl_3$. The main product cut was shown by NMR and GC/MS to be 84% $CF_3CH_2OCF_3$ with 6% $CF_2Cl_2$ and 10% $CFCl_3$ also present, so that 2,2,2-trifluoroethyl trifluoromethyl ether was obtained in 63% yield, 52.7 g.

EXAMPLE 2

2,2,2-Trifluoroethyl Trifluoromethyl Ether
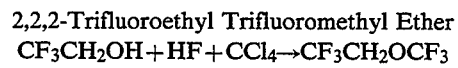

A mixture of 75 g (0.75 mol) of $CF_3CH_2OH$, 230.7 g (1.5 mol) of $CCl_4$, 280 g (14 mol) of HF, and 7 g (0.1 mol) of $BF_3$ were reacted in a metal tube at 100° C. for 8 hours. Volatile crude product isolated as in Example 1 was 3.9 g of a mixture containing mainly $CFCl_3$ with $CF_3CH_2OCF_3$ and $CF_3CH_2OCF_2Cl$ as minor components. The mixture of liquid products insoluble in water (203.8 g) was dried and on analysis by GC and GC/MS found to contain 2.4 g (2% yield) of $CF_3CH_2OCF_3$, 8.8 g (6% yield) of 2,2,2-trifluoroethyl chlorodifluoromethyl ether ($CF_3CH_2OCF_2Cl$), and 47.9 g (57%) of bis(2,2,2-trifluoroethyl) carbonate, along with $CFCl_3$, $CCl_4$ and some bis(2,2,2-trifluoroethyl) ether. Fractionation afforded a sample boiling point 22° to 23° C. indicated by $^1H$ and $^{19}F$ NMR and GC to contain $CF_3CH_2OCF_2Cl$ and $CFCl_3$. A pure cut, boiling point 116° to 118° C., 40.7 g, was identified as bis(2,2,2-trifluoroethyl) carbonate by GC and $^1H$, $^{19}F$ NMR.

EXAMPLE 3

2,2,2-Trifluoroethyl Trifluoromethyl Ether

A Hastelloy ™ nickel alloy tube charged with 75 g (0.75 mol) of trifluoroethanol, 206.1 g (1.50 mol) of $CFCl_3$, 280 g (14 mol) of HF, and 7 g (0.1 mol) of $BF_3$ was heated at 150° C. for 8 hours. The tube was cooled to 25° C., 500 g of distilled water was pumped in, the tube was recooled, and volatile products were transferred under vacuum to a 1 liter stainless steel cylinder. The volatiles (203.4 g) were shown by $^{19}F$ NMR analysis to contain 117.6 g (93%) of 2,2,2-trifluoroethyl trifluoromethyl ether, 74.8 g (36% recovery) of $CFCl_3$, and 10.9 g (6%) of $CF_2Cl_2$.

EXAMPLE 4

2,2,2-Trifluoroethyl Trifluoromethyl Ether
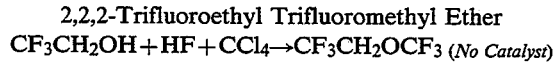

A 1.2-L metal tube charged with 100.0 g (1.0 mol) of trifluoroethanol, 192.3 g (1.25 mol) of $CCl_4$, and 280 g (14 mol) of HF was heated at 150° C. for 8 hours, then cooled to 25° C. Addition of 500 g of water, recooling, and transfer of volatile products under vacuum afforded 144.4 g of a low-boiling mixture. The composition in mol % indicated by $^1H$ and $^{19}F$ NMR analysis was 62.0% $CFCl_3$ (85.5 g), 3.2% $CF_2Cl_2$ (3.9 g), 0.6% $CF_3CH_2OCF_2Cl$ (1.2 g), 17.7% $CF_3CH_2OCF_3$ (29.9 g), 8.9% $CF_3CH_2OCH_2CF_3$ (16.2 g), and 7.6% $CF_3CHF$ (7.8 g).

Water-insoluble liquid products of the reaction weighed 51.8 g. Analysis by GC and by $^1H$ and $^{19}F$ NMR showed it to contain 10.5 g of $CFCl_3$, 0.9 g of $CF_3CH_2OCF_3$, and 39.8 g of $(CF_3CH_2O)_2C=O$. Total conversions were 18% (30.8 g) $CF_3CH_2OCF_3$, 1% (1.2 g) $CF_3CF_2OCF_2Cl$, 8% (7.8 g) $CF_3CH_2F$, 35% (39.8 g) $(CF_3CH_2O)_2C=O$, 12% (16.2 g) $CF_3CH_2OCH_2CF_3$, 3% (3.9 g) $CF_2Cl_2$, and 56% (96.0 g) $CFCl_3$.

EXAMPLE 5

2,2,2-Trifluoroethyl Trifluoromethyl Ether
$(CF_3CH_2O)_2C=O + HF + CCl_4 \rightarrow CF_3CH_2OCF_3$ A mixture of 90.4 g (0.40 mol) of $(CF_3CH_2O)_2C=O$, 230.7 g (1.5 mol) of $CCl_4$, 130 g (6.5 mol) of HF, and 7 g (0.1 mol) of $BF_3$ was heated in a 1.2 liter vessel at 150° C. for 8 hours. The reaction mixture was cooled to 25° C., 500 mL of water was pressured in, the mass was again cooled and volatiles (198.2 g) were transferred under vacuum to a metal cylinder. Liquid product (56.9 g) was collected as a water-insoluble phase and dried over $CaSO_4$. Analysis of these products by GC, GC/MS and NMR showed them to contain $CF_3CH_2OCF_3$ (25% conv.), $CF_3CH_2OC(O)F$ (11% conv.), $CFCl_3$ (67% conv.), and small amounts of $CF_3CH_2OCF_2Cl$, $CF_3CH_2OCF_2OCH_2CF_3$, $CF_3CH_2OCOCl$, $CF_3CH_2OCH_2CF_3$, and $CF_2Cl_2$.

EXAMPLE 6

2,2,2-Trifluoroethyl Trifluoromethyl Ether
$CF_3CH_2OH + HF + COF_2 \rightarrow CF_3CH_2OCF_3$ Reaction of 75 g (0.75 mol) of $CF_3CH_2OH$, 130 g (6.5 mol) of HF, 132 g (2.0 mol) of $COF_2$, and 7 g (0.1 mol) of $BF_3$ under pressure at 150° C. for 8 hours, followed by quenching with 500 mL of water gave 70.0 g of volatile products and 3 g of liquid products. Analysis by GC, GC/MS and NMR indicated that a 27% conv. to $CF_3CH_2OCF_3$, 28% conv. to $CF_3CH_2OC(O)F$, 7% conv. to $CF_3CH_2F$, and 3% conv. to $(CF_3CH_2O)_2C=O$ had been attained.

EXAMPLE 7

2,2,2-Trifluoroethyl Trifluoromethyl Ether
$CF_3CH_2OH + HF + COCl_2 \rightarrow CF_3CH_2OCF_3$ A 1.3 liter metal tube charged with 35 g (0.35 mol) of $CF_3CH_2OH$, 130 g (6.5 mol) of HF, 71 g (0.72 mol) of $COCl_2$, and 7 g (0.1 mol) of $BF_3$ was heated at 150° C. for 10 hours. Water (500 g) was pressured into the cooled tube, and volatiles (23.2 g) were transferred under vacuum to a metal cylinder. Analysis of the volatile product by $^1H$ and $^{19}F$ NMR showed that 22.3 g (38%) of $CF_3CH_2OCF_3$ and 0.9 g (3%) of $CF_2CH_2F$ were present with traces of $CF_3CH_2OC(O)Cl$ and $(CF_3CH_2O)_2C=O$.

EXAMPLE 8

Trifluoromethyl 2,2,3,3-Trifluoropropyl Ether
$HCF_2CF_2CH_2OH + HF + CCl_4 \rightarrow HCF_2CF_2CH_2OCF_3$ A 1.2 liter tube charged with 66.0 g (0.50 mol) of $HCF_2CF_2CH_2OH$, 192 g (1.25 mol) of $CCl_4$, 250 g (12.5 mol) of HF, and 7 g (0.1 mol) of $BF_3$ was held at 150° C. for 8 hr. Water (300 mL) was pumped into the cooled reactor, which was recooled to 25° C. The water-insoluble liquid product (63 g) was separated, dried over $CaSO_4$, and distilled to afford 22.6 g (23%) of trifluoromethyl 2,2,3,3-tetrafluoropropyl ether, boiling point 45.9° to 46.3° C., identified by GC, GC/MS, IR, and NMR. GC indicated that the crude product contained 41.5 g (41% conv.) of $HCF_2CF_2CH_2OCF_3$.

EXAMPLE 9

Trifluoromethyl 2-Chloro-2,2-difluoroethyl Ether
$ClCF_2CH_2OH + HF + CCl_4 \rightarrow ClCF_2CH_2OCF_3$ A reaction of 58.3 g (0.50 mol) of $ClCF_2CH_2OH$, 192 g (1.25 mol) of $CCl_4$, 280 g (14 mol) of HF, and 7 g (0.1 mol) of $BF_3$ was carried out as described for Example 8. The liquid product (18.7 g) was determined by GC and GC/MS to contain 2.4 g (3%) of $ClCF_2CH_2OCF_3$.

EXAMPLE 10

2,2,2-Trifluoroethyl Trifluoromethyl Ether
$CF_3CH_2OH + HF + CCl_4 \rightarrow CF_3CH_2OCF_3$ A 1.3 liter Hastelloy ™ nickel alloy tube charged with 30 g (0.10 mol) of $SbCl_5$ and 280 g (14 mol) of HF was agitated at 60° C. for 1 hr, then cooled. A mixture of 100 g (1.0 mol) of $CF_3CH_2OH$ and 192.3 g (1.25 mol) of $CCl_4$ was pressured in, and the tube was heated at 100° C. for 8 hours. The reactor was cooled, 500 g of water was pumped in, the reactor was cooled again to 30° C., and then volatile products (115 g) were transferred under vacuum to a metal cylinder. Liquid product (54 g) was collected separately. Analyses by GC and NMR showed the presence of 15.5 g (9%) of $CF_3CH_2OCF_3$, large amounts of $(CF_3CH_2O)_2C=O$ and $CFCl_3$, with small amounts of $CF_3CH_2OCF_2Cl$, $CF_2Cl_2$, and $CF_3CH_2OCH_2CF_3$ also present.

EXAMPLE 11

2,2,2-Trifluoroethyl Trifluoromethyl Ether $B_2O_3$ as Catalyst

A metal tube charged with 3.5 g (0.05 mol) of $B_2O_3$, 100.0 g (1.0 mol) of $CF_3CH_2OH$, 192.3 g (1.25 mol) of $CCl_4$, and 280 g (14 mol) of HF was agitated for 10 hr at 150° C. Water, 500 mL, was added to the tube, and 120.1 g of volatile product was transferred out after cooling to 30° C. Analysis by GC and $^1H$ and $^{19}F$ NMR showed the presence of 99.7 g (59%) of $CF_3CH_2OCF_3$ along with $CFCCl_3$ and very small amounts of other products.

EXAMPLE 12

2,2,2-Trifluoroethyl Trifluoromethyl Ether $TaF_5$ as Catalyst

A 100 mL Inconel ™ nickel alloy tube containing a magnetic stirrer, an internal thermocouple and equipped with a condenser, back-pressure regulator, and an on-line analytical system was charged with $TaF_5$ (8.0 g, 0.03 mol). The reactor was then cooled, evacuated and charged with $CF_3CH_2OH$ (8.0 g, 0.08 mol), $CCl_4$ (24 g, 0.16 mol) and anhydrous HF (5 mL, 0.25 mol). The reactor was then pressurized with nitrogen (200 psig, 1480 kPa) and gradually heated to 150° C. with stirring. The back-pressure regulator was set at 500 psig (3550 kPa). After 2 hours at 150° C., the reaction was stopped and the reactor contents analyzed by GC. The results in area % were as follows:, $CF_3CH_2OCF_3$ (54.4%), $(CF_3CH_2O)_2C=O$ (0.3%), $CCl_4$ (0.1%), $CCl_3F$ (2.5%), $CCl_2F_2$ (19.8%), $CClF_3$ (1.2%), $CHCl_2CF_3$ (0.3%), $CH_2ClCF_3$ (0.9%) and $CH_2FCF_3$ (20.0%).

EXAMPLE 13

2,2,2-Trifluoroethyl Trifluoromethyl Ether Purification

A 105 g portion of the reaction product from the reaction of $CF_3CH_2OH$, $CCl_4$ and HF containing 85% $CF_3CH_2OCF_3$ and 15% $CFCl_3$ and trace impurities was purified according to the herein described procedure. The reaction product was treated with 120 g $Na_2S.9-H_2O$ dissolved in 500 mL of dimethyl formamide at 100° C. for 10 hours. After cooling to room temperature, the solution was passed successively through 10% aqueous potassium hydroxide, 10% sulfuric acid and finally through a tube containing anhydrous calcium sulfate. The purified product was found by GC analysis to be essentially pure $CF_3CH_2OCF_3$ and trace impurities. $^1H$ and $^{19}F$ NMR showed the purified product to contain $CF_3CH_2OCF_3$, <1% $CF_3CH_2F$ and trace amounts of $CF_2Cl_2$. This purification was necessary because of the difficulty in separating $CFCl_3$ from $CF_3CH_2OCF_3$ by distillation.

EXAMPLE 14

$(CF_3)_2CHOH + HF + CCl_4 \rightarrow (CF_3)_2CHOCF_3 + (CF_3)_2CHOCF_2Cl + (CF_3)_2CHOCFCl_2 + (CF_3)_2CHOCF_2OCH(CF_3)_2$ A 1.3 liter Hastelloy ™ nickel alloy tube charged with 168 g (1.0 mol) of hexafluoroisopropanol, 192.3 g (1.25 mol) of $CCl_4$, 280 g (14 mol) of HF, and 10 g of $BF_3$ was heated at 150° C. for 10 hours. The tube was then cooled to 25° C., 500 g of water was pumped in, and the tube was cooled again. Volatile products (150.2 g) transferred under vacuum were a mixture indicated by GC to contain 11.4 g of $CF_2Cl_2$, 2.7 g of $(CF_3)_2CHOCF_3$, 48.7 g of $CFCl_3$, 79.5 g of $(CF_3)_2CHOCF_2Cl$, 2.7 g of $(CF_3)_2CHOCFCl_2$, and 5.3 g of $(CF_3)_2CHOCF_2OCH(CF_3)_2$. Water-insoluble liquid product (106.3 g) was shown by GC and GC/MS analysis to contain 0.5 g of $CF_2Cl_2$, 0.6 g of $(CF_3)_2CHOCF_3$, 10.0 g of $CFCl_3$, 63.6 g of $(CF_3)_2CHOCF_2Cl$, 4.5 g of $(CF_3)_2CHOCFCl_2$, and 27.1 g of $(CF_3)_2CHOCF_2OCH(CF_3)_2$. Combining, the totals obtained were 3.3 g (1.4% yield) of $(CF_3)_2CHOCF_3$, 143.1 g (57%) of $(CF_3)_2CHOCF_2Cl$, 7.2 g (2.7%) of $(CF_3)_2CHOCFCl_2$, and 32.4 g (17%) of $(CF_3)_2CHOCF_2OCH(CF_3)_2$.

Fractionation of the combined products afforded 23.2 g of a mixture, boiling point up to 39.5° C., shown by $^1H$ and $^{19}F$ NMR and GC to contain mainly $CFCl_3$ and $(CF_3)_2CHOCF_2Cl$ along with a small amount of trifluoromethyl 1,1,1,3,3,3-hexafluoro-2-propyl ether. There was then distilled 120.1 g, boiling point 40° to 45° C., identified by GC and NMR as chlorodifluoromethyl 1,1,1,3,3,3-hexafluoro-2-propyl ether. Next came 2.7 g, boiling point 75° to 79° C., of dichlorofluoromethyl 1,1,1,3,3,3-hexafluoro-2-propyl ether, identified by GC and NMR. Finally, there was obtained 24.4 g of 2,6-bis(-trifluoromethyl)1,1,1,4,4,7,7,7-octafluoro-3,5-dioxaheptane, $((CF_3)_2CHOCF_2OCH(CF_3)_2)$, boiling point 89° to 94° C. identified by GC and NMR analyses. NMR and mass spectroscopic (MS) analyses of $(CF_3)_2CHOCF_2OCH(CF_3)_2$ are as follows: $^1H$-NMR $(CDCl_3)$ δ 4.78 (septet, $J_{HF}$, 5.4 Hz, $OCH(CF_3)_2$); $^{19}F$-NMR $(CDCl_3)$ φ −60.9 (m, 2F, $OCF_2O$), −74.3 (m, 12F, $CF_3$). MS, m/e 364.966156 (M+-F; mass meas. $C_7H_2F_{13}O_2$), 314.9808 (M+-$CF_3$), 216.983002 (mass meas. $(CF_3)_2CHOCF_2^+$), 150.9758 ($CF_3CHCF_3^+$).

EXAMPLE 15

$(CF_3)_2CHOH + HF + CCl_4 \rightarrow (CF_3)_2CHOCF_3 + (CF_3)_2CHOCF_2Cl + (CF_3)_2CHOCFCl_2 + (CF_3)_2CHOCF_2OCH(CF_3)_2$ A mixture of 143 g (0.85 mol) of $(CF_3)_2CHOH$, 169 g (1.1 mol) of $CCl_4$, 240 g (12 mol) of HF, and 10 g of $BF_3$ was heated in a 1.3 liter tube for 8 hours at 150° C., then for 4 hours at 180° C. Water (500 g) was added to the cooled mixture, and volatiles (163 g) and water-insoluble liquid (75.3 g) were isolated as before. Analyses by GC and NMR showed the product to contain 28.1 g of $CF_2Cl_2$, 9.0 g (4.5% conv. to) of $(CF_3)_2CHOCF_3$, 40.0 g of $CFCl_3$, 141.0 g (66%) of $(CF_3)_2CHOCF_2Cl$, 1.7 g (1%) of $(CF_3)_2CHOCFCl_2$, and 18.5 g (11%) of $(CF_3)_2CHOCF_2OCH(CF_3)_2$.

Reaction at higher temperature than the Example 14 led to a higher conversion to the trifluoromethyl ether.

EXAMPLE 16

Trifluoromethyl Methyl Ether
$CH_3OH + HF + CCl_4 \rightarrow CH_3OCF_3$ (No Catalyst)

A 1L Hastelloy ™ nickel alloy tube charged with 32.0 g (1.0 mol) of methanol, 153.8 g (1.0 mol) of $CCl_4$, and 120 g (6.0 mol) of HF was heated at 100° C. for 10 hours, then cooled to 25° C. Addition of 500 g of water, recooling, and transfer of volatile products under vacuum afforded 5.3 g of a low-boiling mixture. Analysis by GC/MS showed the product mixture to contain, $CH_3F$, $CH_3Cl$, $CH_3OCH_3$, $CH_3OCF_3$, $CFCl_3$ and $CCl_4$.

What is claimed is:

1. A product comprising a bis-ether of the formula $(CF_3(CF_2)_m)_2CHOCF_2OCH((CF_2)_mCF_3)_2$ wherein m is an integer from 0 to 3, produced by a process comprising reacting a first reactant of the formula $(CF_3(CF_2)_m)_2CHOH$ with $CCl_4$ and HF to produce $(CF_3(CF_2)_m)_2CHOCF_3$ and said bis-ether.

2. A bis-ether compound of the formula $(CF_3(CF_2)_m)_2CHOCF_2OCH((CF_2)_mCF_3)_2$, wherein m is an integer from 0 to 3.

3. The bis-ether compound in accordance with claim 2 having the formula $(CF_3)_2CHOCF_2OCH(CF_3)_2$.

4. A product comprising a bis-ether of the formula $(CF_3(CF_2)_m)_2CHOCF_2OCH((CF_2)_mCF_3)_2$, wherein m is an integer from 0 to 3, produced a process comprising reacting a first reactant of the formula $(CF_3(CF_2)_m)_2CHOH$, with $CCl_4$ and HF in the presence of a catalyst selected from the group consisting of $SbX_5$, $AsX_5$, $TaX_5$, $BX_3$, $NbX_5$ and $PX_5$, wherein each X is independently selected from Cl and F, to produce $(CF_3(CF_2)_m)_2COCF_3$ and said bis-ether.

* * * * *